United States Patent
Avanzino et al.

(10) Patent No.: US 7,981,109 B2
(45) Date of Patent: Jul. 19, 2011

(54) SYSTEM AND METHOD FOR A USER INTERFACE

(75) Inventors: Paul Avanzino, Tustin, CA (US); Raphael Gordon, Ladera Rancy, CA (US); Dan Teodorescu, Fountain Valley, CA (US); Ahmad Salehi, Irvine, CA (US)

(73) Assignee: Novartis AG, Basel (CH)

( * ) Notice: Subject to any disclaimer, the term of this patent is extended or adjusted under 35 U.S.C. 154(b) by 208 days.

(21) Appl. No.: 11/838,973

(22) Filed: Aug. 15, 2007

(65) Prior Publication Data

US 2009/0048587 A1 Feb. 19, 2009

(51) Int. Cl.
*A61B 17/00* (2006.01)

(52) U.S. Cl. .................. 606/1; 606/10; 351/211

(58) Field of Classification Search ....... 606/1; 351/211
See application file for complete search history.

(56) References Cited

U.S. PATENT DOCUMENTS

| | | | |
|---|---|---|---|
| 4,202,037 A * | 5/1980 | Glaser et al. | 345/632 |
| 4,544,243 A | 10/1985 | Munnerlyn | |
| 4,870,964 A * | 10/1989 | Bailey et al. | 606/6 |
| 4,907,589 A * | 3/1990 | Cosman | 606/34 |
| 5,028,802 A | 7/1991 | Webb et al. | |
| 5,206,672 A | 4/1993 | Rowe | |
| 5,303,085 A | 4/1994 | Rallison | |
| 5,308,355 A | 5/1994 | Dybbs | |
| 5,450,143 A | 9/1995 | Rowe et al. | |
| 5,455,766 A | 10/1995 | Scheller et al. | |
| 5,545,160 A | 8/1996 | O'Rourke | |
| 5,549,597 A | 8/1996 | Shimmick et al. | |
| 5,619,377 A | 4/1997 | Rallison | |
| 5,642,227 A | 6/1997 | Rallison | |
| 5,673,151 A | 9/1997 | Rallison | |
| 5,674,233 A | 10/1997 | Dybbs | |
| 5,969,791 A | 10/1999 | Rowe | |
| 5,991,087 A | 11/1999 | Rallison | |
| 5,997,528 A | 12/1999 | Bisch et al. | |
| 6,066,129 A | 5/2000 | Larson | |
| 6,078,681 A | 6/2000 | Silver | |
| 6,087,941 A | 7/2000 | Ferraz | |
| 6,106,512 A | 8/2000 | Cochran et al. | |
| 6,149,643 A | 11/2000 | Herekar et al. | |
| 6,159,205 A | 12/2000 | Herekar et al. | |
| 6,193,710 B1 | 2/2001 | Lemberg | |

(Continued)

FOREIGN PATENT DOCUMENTS

WO WO 98/08442 A1 3/1998

(Continued)

*Primary Examiner* — Henry M Johnson, III
*Assistant Examiner* — Jeffrey B Lipitz

(57) ABSTRACT

Embodiments of systems and methods for an interface for providing a user with feedback are presented. Specifically, embodiments of such an interface may include a head-up display unit which is mounted on a microscope utilized by a user when performing a surgical procedure. The heads-up display unit may include an eye-piece ring which is fitted onto or in one of the eye pieces of the microscope. The heads-up unit receives data regarding one or more parameters from a surgical console or other source and produces audio or visual feedback corresponding to a desired parameter. Any visual feedback produced may then be propagated to the eye piece ring allowing a user of the microscope to obtain the feedback when performing a surgical procedure utilizing the microscope and obviating the need to look at a screen of the surgical console to obtain such feedback. Thus, feedback is provided to a user in a non-intrusive manner such that the user can obtain this feedback without distracting from a surgical procedure.

22 Claims, 4 Drawing Sheets

U.S. PATENT DOCUMENTS

| | | | |
|---|---|---|---|
| 6,251,113 B1* | 6/2001 | Appelbaum et al. | 606/107 |
| 45,887 A1 | 4/2002 | DeHoogh et al. | |
| 6,394,999 B1 | 5/2002 | Williams et al. | |
| 6,485,413 B1 | 11/2002 | Boppart et al. | |
| 6,491,686 B2 | 12/2002 | Lemberg | |
| 6,512,530 B1 | 1/2003 | Rzepkowski et al. | |
| 6,583,796 B2 | 6/2003 | Jamar et al. | |
| 6,623,429 B2 | 9/2003 | Percival et al. | |
| 6,669,340 B2 | 12/2003 | Percival et al. | |
| 6,671,535 B1 | 12/2003 | McNichols et al. | |
| 24,384 A1 | 2/2004 | Novak | |
| 6,726,625 B2 | 4/2004 | Luce | |
| 6,749,302 B2 | 6/2004 | Percival et al. | |
| 6,783,523 B2 | 8/2004 | Qin et al. | |
| 6,816,316 B2 | 11/2004 | Caudle et al. | |
| 6,908,196 B2 | 6/2005 | Herekar et al. | |
| 6,945,650 B2 | 9/2005 | Beverly | |
| 7,001,018 B1* | 2/2006 | Martin | 351/211 |
| 2002/0047990 A1* | 4/2002 | Fergason et al. | 351/208 |
| 2003/0073980 A1 | 4/2003 | Finlay et al. | |
| 2004/0102799 A1 | 5/2004 | Perez et al. | |
| 2005/0277913 A1* | 12/2005 | McCary | 606/1 |
| 2006/0114175 A1 | 6/2006 | Boukhny | |
| 2006/0236242 A1 | 10/2006 | Boukhny et al. | |
| 2006/0247659 A1 | 11/2006 | Moeller et al. | |
| 2007/0008624 A1* | 1/2007 | Hirayama | 359/630 |
| 2007/0081078 A1* | 4/2007 | Cummings et al. | 348/79 |
| 2008/0085499 A1* | 4/2008 | Horvath | 434/262 |
| 2008/0243142 A1* | 10/2008 | Gildenberg | 606/130 |
| 2009/0049397 A1 | 2/2009 | Boukhny | |
| 2009/0303315 A1* | 12/2009 | Charlesworth | 348/61 |

FOREIGN PATENT DOCUMENTS

| | | |
|---|---|---|
| WO | WO 02/32354 A1 | 4/2002 |
| WO | WO 2005/084570 A1 | 9/2005 |
| WO | WO 2006/060423 A1 | 6/2006 |
| WO | WO 2009/023408 A1 | 2/2009 |

* cited by examiner

SYSTEM AND METHOD FOR A USER INTERFACE

BACKGROUND

The present invention relates to surgical systems. More particularly, embodiments of the present invention relate to ophthalmic surgical systems. Even more particularly, embodiments of the present invention relate to interfaces for use with ophthalmic surgical systems.

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. Such surgical instrumentation can comprise a Vitreoretinal and Cataract microsurgical console. Such a surgical console can provide a variety of functions depending on the surgical procedure and surgical instrumentation. For example, surgical consoles can expedite cataract surgeries (e.g. phacoemulsification procedures) by helping manage irrigation and aspiration flows into and out of a surgical site. And of course surgical consoles can provide other functions.

Thus, Vitreoretinal and Cataract surgical consoles usually have a large set of functionality, such as vitreous cutting, vacuum, etc. and commensurately are amenable to a large degree of customization. In other words, each of the parameters of such a surgical console may be individually adjusted to achieve desired settings. While at first blush this myriad number of configuration permutations might seem to be advantageous this ability may, however, in many cases cause a whole host of problems. For example, doctors may have to adjust each of multiple parameters individually during the course of performing a surgery, consuming valuable time. Furthermore, the adjustment of these parameters may need to be coordinated (e.g. the setting of one parameter depends at least in part on the settings of one or more other parameters) for best performance or to avoid possible injury or complications. This requirement may mean that settings corresponding to multiple parameters may need to be verified, calculated or adjusted even if a doctor is concerned only with a single parameter. Not only do these adjustments consume more time, but in addition, they may increase the chances of mistakes being made in the configuration of the surgical console, which, in some instances, may lead to injury of a patient or a doctor performing a surgical procedure. Additionally, feedback regarding these parameters, or other parameters associated with the operation of the surgical console, surgical procedure, patient, etc. may need to be provided to a user substantially in real time during operation of such a surgical console.

Therefore there is a need for interfaces for use with a surgical console.

SUMMARY OF THE INVENTION

Embodiments of systems and methods for an interface for providing a user with feedback are presented. Specifically, embodiments of such an interface may include a head-up display unit which is mounted on a microscope utilized by a user when performing a surgical procedure. The heads-up display unit may include an eye-piece ring which is fitted onto or in one of the eye pieces of the microscope. The heads-up unit receives data regarding one or more parameters from a surgical console or other source and produces audio or visual feedback corresponding to a desired parameter. Any visual feedback produced may then be propagated to the eye piece ring allowing a user of the microscope to obtain the feedback when performing a surgical procedure utilizing the microscope and obviating the need to look at a screen of the surgical console to obtain such feedback. Thus, feedback is provided to a user in a non-intrusive manner such that the user can obtain this feedback without distracting from a surgical procedure.

More particularly, in one embodiment the visual feedback provided may be congruent with, or correspond to, an interface which was utilized to configure the parameter on which feedback is being provided or which was used to configure an associated parameter. Thus, by correlating the visual feedback provided through the heads-up display with an interface used to configure the surgical console an easy mnemonic device is provided for a user to remember the meaning of the provided visual feedback.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

A more complete understanding of the present invention and the advantages thereof may be acquired by referring to the following description, taken in conjunction with the accompanying drawings in which like reference numbers indicate like features and wherein.

DETAILED DESCRIPTION

Preferred embodiments of the invention are illustrated in the FIGURES, like numerals being used to refer to like and corresponding parts of the various drawings.

Figure 1:
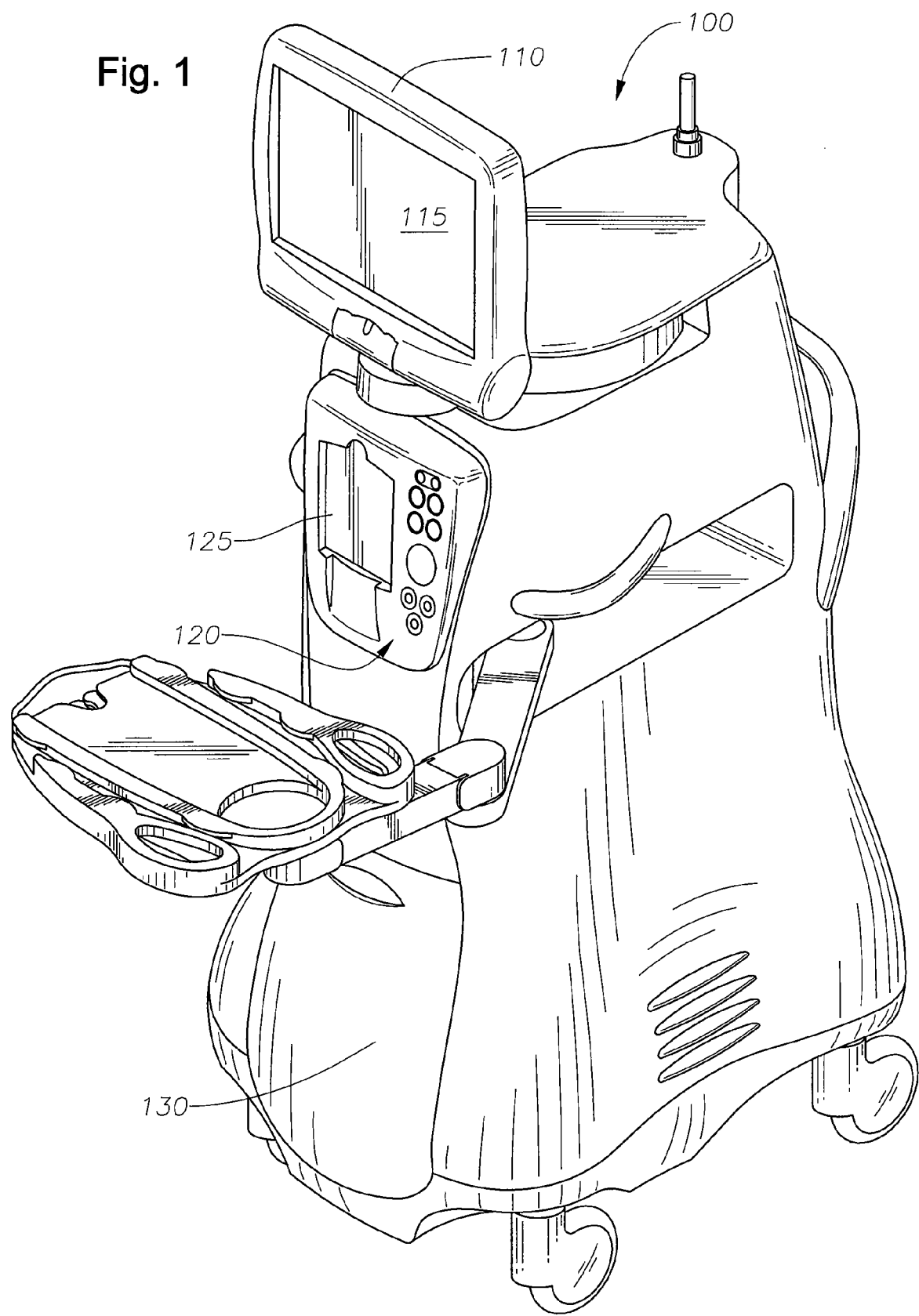
FIG. 1 is a diagrammatic representation of one embodiment of a surgical console.

Before elaborating on various embodiments of the present invention it may be helpful to illustrate surgical console with which embodiments of the present invention may be utilized. FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a GUI that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features.

Surgical console 100 is provided by way of example and embodiments of the present invention can be implemented with a variety of surgical systems. Example surgical systems in which various embodiments of the present invention can be used include, for example, the Series 2000® Legacy® cataract surgical system, the Accurus® 400VS surgical system, the Infiniti™ Vision System surgical system available from Alcon Laboratories Inc. of Fort Worth, Tex. Embodiments of the present invention can be implemented in other suitable surgical systems having a touch screen as would be understood by one of ordinary skill in the art.

In operation, a Graphical User Interface (GUI) may be displayed on screen 115, such that a user may interact with the surgical console 100. In one embodiment, the GUI for surgical system may allow a user to modally interact with surgical console 100. In other words, the GUI may present a user of surgical console 100 a set of icons or buttons corresponding to the entire range of functionality of surgical console 100 where the user can select from these function icons in order to utilize a particular functionality of surgical console 100. The user can then configure any parameters or sub-modes for the desired functionality and utilize this functionality. Thus, during a surgical procedure, for each step of the surgical procedure a user will interact with surgical console 100 to select the functionality desired for the step and configure any parameters or sub-modes for the step. As can be seen then, modal interaction with surgical console 100 may require a relatively large number of inputs (e.g. from foot pedal control or touch screen 115) to implement a surgical procedure and the GUI (or other method of interaction) with surgical console 100 may be quite cluttered and busy as it presents the user with a wide variety of options corresponding to the entire range of functionality of surgical console 100.

Figure 2:
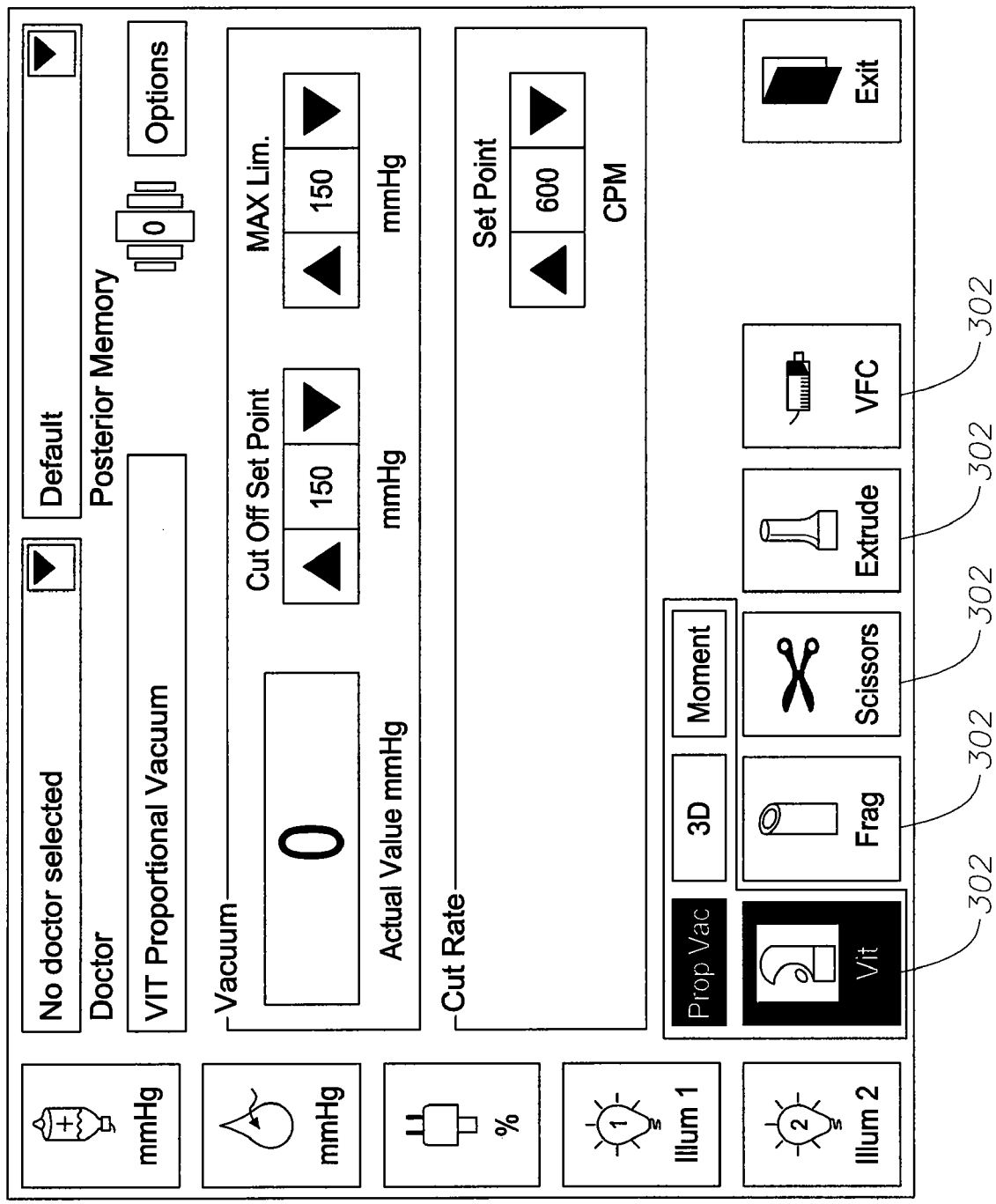
FIG. 2 is a representation of one embodiment of a graphical user interface (GUI).

For example, surgical console 100 may include functionality for vitreous cutting (Vit), vacuum (Extraction), Scissors, Viscous Fluid Control (VFC), ultrasonic lens removal (Fragmatome) and user feedback. One embodiment of a GUI for modal based interaction with such a surgical console 100 is depicted in FIG. 2. Notice that GUI 300 presents icons 302 where each of icons 302 corresponds to one function of surgical console 100. Consequently, to utilize functionality represented by icons 302 a user of surgical console 100 may select the desired icon 302. To implement a surgical procedure then, for each step the icon 302 representing functionality desired for that step may be selected, and any parameters or sub-modes for that functionality configured. At every subsequent step of the surgical procedure where functionality of surgical console 100 is desired the user must again select the desired functionality corresponding to the step from icons 202 and configure any parameters or sub-modes. As may be imagined this is an inefficient method of interacting with surgical console, as extraneous interactions are needed to select and utilize desired functionality.

What is desired then is a simple method of interacting with, and configuring, a surgical console. Thus in some cases, a simplified user interface may be utilized which allows a user to control two or more parameters through a single control field or region of a screen. Interfaces of this type may be color coded to enhance the user's perception of the controls, status, safety, performance, etc. of the surgical console 100 or a surgical procedure. For example, a two-dimensional interface can be presented to the user. The cells corresponding to various combinations of parameters can be color coded to reflect expected increase in temperature which is approximately proportional to the amount of ultrasound and inversely proportional to the flow rate. Thus, in one embodiment, higher ultrasound values corresponding to low flow rates may be color coded as "hotter" colors (e.g. red or orange), while lower ultrasound values and higher flow rater can be color coded as "colder" colors (e.g. blue or green) as presented in the table of FIG. 3.

Figures 3, 4:
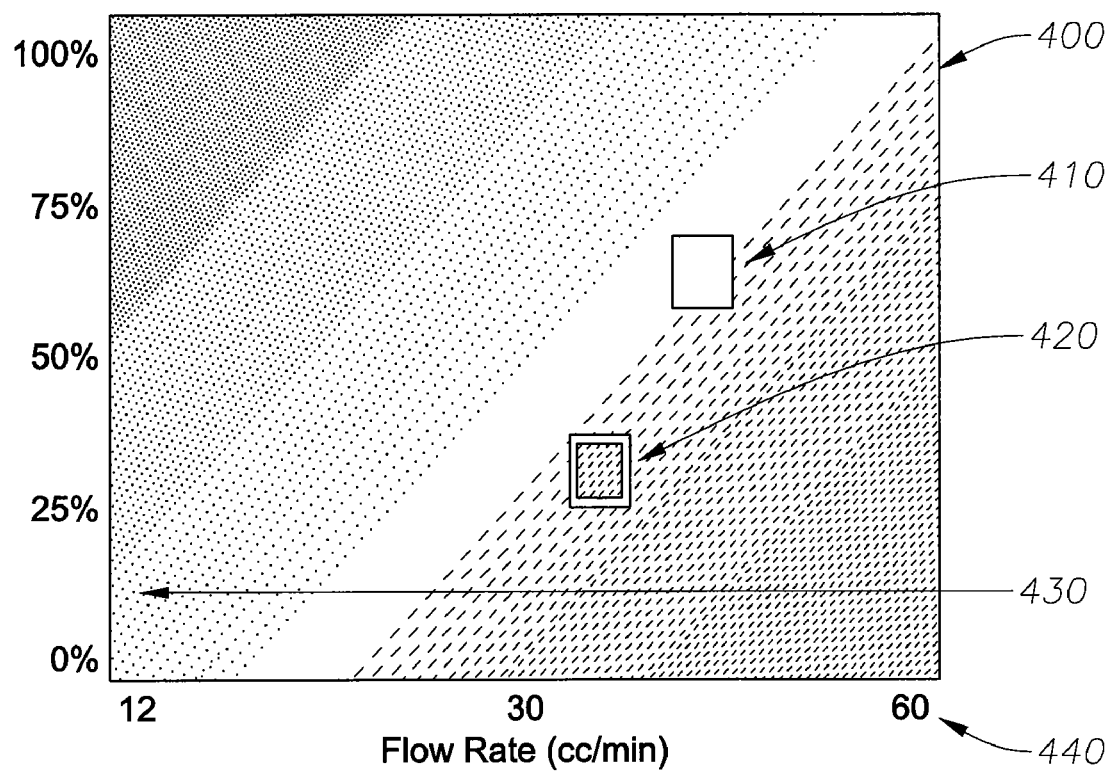
FIG. 3 is a representation of one embodiment of a color palette.
FIG. 4 is a representation of one embodiment of a graphical user interface (GUI).

One embodiment of just such an interface is depicted in FIG. 4. Control field 400 may be presented to allow a user to control instantaneous average power 430 and instantaneous flow rate 440. More particularly in field 400, the blue-red gradient is an estimation of incision temperature increase after a duration (which may be specified by a user or otherwise specified). Blue represents a lower temperature increase while red indicates a greater temperature increase. A user may control the field by dragging a requested settings icon 410 and is given real time feedback through a similar looking current settings icon 420 which also indicates an instantaneous incision temperature (e.g. based on foot switch penetration).

Thus, feedback is provided to a user of surgical console 100 (e.g. instantaneous incision temperatures) through touch screen interface 115. The visual indicators presented on touch screen 115 may, however, require a user to look up and away from surgery. While audio feedback may be used (e.g. sound emitted by surgical console 100) to indicate real time status of one or more parameters the use of these audio indicators may require a user to remember the meaning of multiple sounds and may get lost in the background noise of an operating room.

Therefore, it would be desirable to provide feedback regarding one or more parameters in a non-intrusive manner such that a user can obtain this feedback without distracting from a surgical procedure or requiring a user to look way from the surgical procedure to obtain this feedback. To that end, attention is now directed to systems and methods for an interface for providing a user with feedback. Specifically, embodiments of such an interface may include a head-up display unit which is mounted on a microscope utilized by a user when performing a surgical procedure. The heads-up display unit may include an eye-piece ring which is fitted onto or in one of the eye pieces of the microscope. The heads-up unit receives data regarding one or more parameters from a surgical console or other source and produces audio or visual feedback corresponding to the desired parameters. Any visual feedback corresponding to a desired parameter may then be propagated to the eye piece ring allowing a user of the microscope to obtain the feedback when performing a surgical procedure utilizing the microscope and obviating the need to look at a screen of the surgical console to obtain such feedback.

More particularly, in one embodiment the visual feedback provided may be congruent with, or correspond to, an interface which was utilized to configure the parameter on which feedback is being provided or which was used to configure an associated parameter. Thus, by correlating the visual feedback provided through the heads-up display with an interface used to configure the surgical console an easy mnemonic device is provided for a user to remember the meaning of the provided visual feedback.

Figure 5:
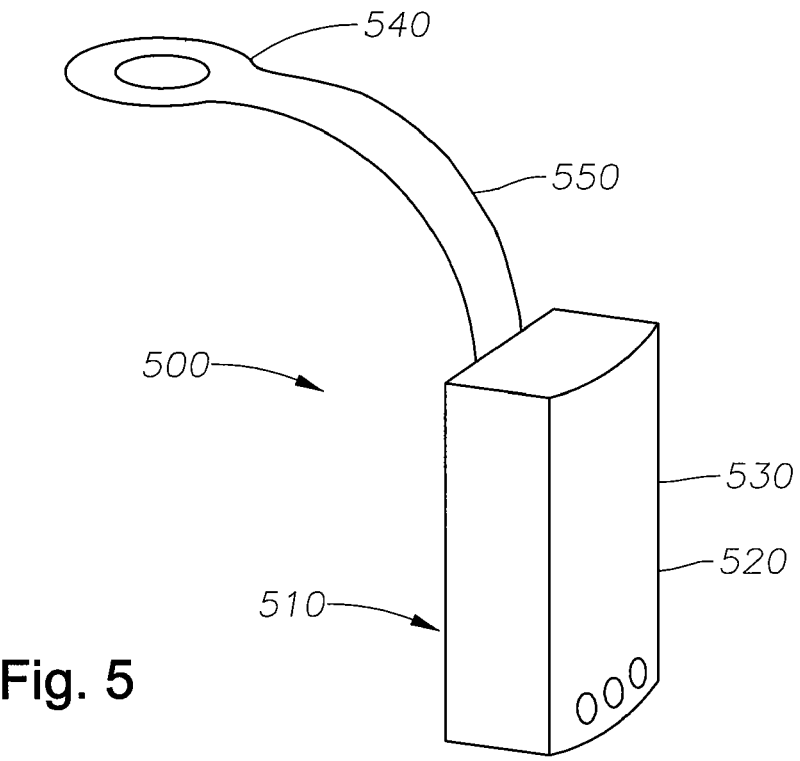
FIG. 5 is a representation of one embodiment of a heads-up display.

Turning now to FIG. 5, one embodiment of a head-up display unit for use with a microscope is depicted. Heads-up display unit 500 may comprise body 510 which may be configured to mount to a microscope used in performing surgical procedures or another ophthalmologic instrument. Body 510 may, in turn, comprise a wired and/or wireless transceiver 520 to communicate with, for example, surgical console 100 or another source of data, a speaker 530 to produce audio output. A set of indicator LED lights (not shown), or another light source, operable to produce at least a portion, if not substantially the whole spectrum of, visible light and which may further be operable to produce a variety of light patterns (e.g. blink rates of a single color, alternating patterns of colors, blink rates of multiple colors, etc.). Heads-up display unit 500 may also comprise eye-piece ring 540 which may made from a translucent rubber or polymer operable to conduct light. Eye-piece ring 540 may be coupled to body 510 of heads-up display 500 by flexible guide 550 which may be made of translucent rubber, polymer, plastic film or light pipe such that light produced by the set of indicator LED lights is conducted to eye-piece ring 540. Light guide 550 may also be shielded or otherwise surrounded to block out interference from ambient light. Eye-piece 540 ring is configured to be fitted into, onto, or be the eye-piece of a microscope with which heads-up display 500 is being utilized such that light produced by the set of LED indicator lights and conducted by guide 550 may be presented in the eye-piece of the microscope through eye-piece ring 540.

Figure 6:
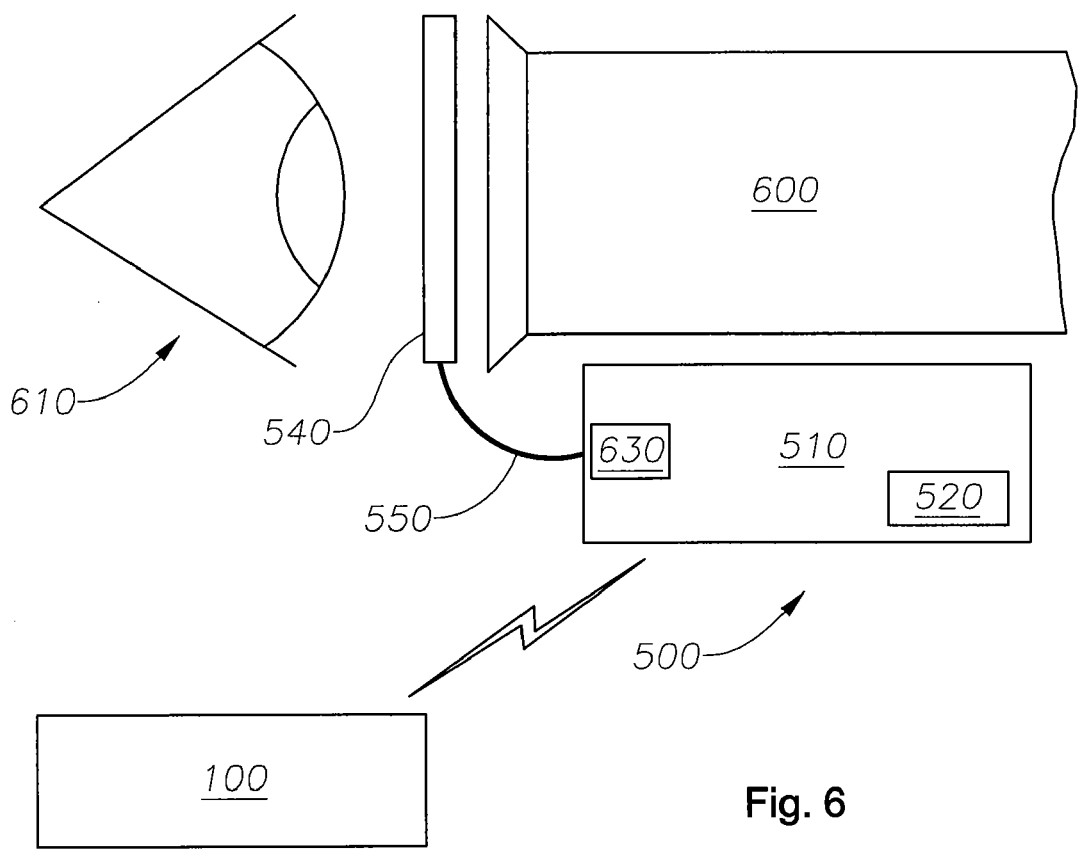
FIG. 6 is a representation of one embodiment of the use of a heads-up display.

Moving now to FIG. 6, a representation of the use of heads-up display 500 during a surgical procedure is depicted. Before a surgical procedure, user 610 may configure parameters of surgical console 100 utilizing one or more interfaces (e.g. such as the interface depicted above with respect to FIG. 4). User 610 may also configure surgical console 100 to provide feedback on one or more surgical parameters (which may be parameters which change, or are measured or calculated, one or more times during a surgical procedure) through heads-up display 510 and correspondingly, how feedback regarding these surgical parameters is to be provided (e.g. audio feedback, visual feedback, the configuration of the audio feedback, such as beep rate, colors of light to utilize in providing visual feedback, blink rate of visual feedback, intensity of light of the visual feedback, etc.) The color of the visual feedback can be correlated to the value of a surgical parameter measured by the console, for example ultrasound power or vacuum level, or it could be correlated to a calculated value, for example estimated temperature at the incision. Correlation may also be pre-defined or user defined. For example, a user can be presented with a color spectrum and allowed to assign blue to the minimum parameter and red to the maximum parameter and all colors in between will be interpolated to the parameter range according to the color wavelength. Furthermore, the color of the visual feedback may be correlated to a user interface used to configure the parameter.

During a surgical procedure then, data on these configured surgical parameters (and, in one embodiment data on how to present these various surgical parameters) may be transmitted from surgical console 100 to transceiver 520 on heads-up display 500. Heads-up display 500 will then produce the corresponding feedback for each of these configured surgical parameters. Any visual feedback produced by heads-up display 500 (e.g. by set of LED lights 630) may be conducted throughout guide 550 to eye-ring 540 fitted on microscope eye-piece 600 such that user 610 may be presented with this visual feedback without having to look away from microscope eye-piece 600 or the surgical procedure he is conducting.

For example, with respect to the interface depicted above in FIG. 4, a color corresponding to a color of control field 400 may be utilized to reflect the surgical parameter of estimated instantaneous incision temperature such that the color associated with status indicator 420 may be presented to a user through eye-piece ring 540 during a surgical procedure while a blink rate or pattern of this visual feedback may indicate vacuum level ranges.

It will be noted from a reading of the above description that an almost endless variety of information about different surgical parameters may be presented to a user using different types or configurations of feedback. For example, feedback regarding one parameter may be presented using one color palette during a first time period, feedback regarding another parameter may be provided using a second color palette during a second time period, feedback regarding a third parameter may be provided using a blink rate of the color palette during the first time, feedback regarding a fourth parameter may be provided using a blink rate of the visual feedback being provided during the second time, feedback on a fifth parameter may be presented using audio feedback etc. Many more permutations may be possible, as may be imagined, though practically the amount of feedback presented using heads-up display 500 may be limited by the ability of a surgeon to comprehend or remember the meaning of the feedback presented.

Although the present invention has been described in detail herein with reference to the illustrated embodiments, it should be understood that the description is by way of example only and is not to be construed in a limiting sense. It is to be further understood, therefore, that numerous changes in the details of the embodiment of this invention and additional embodiments of this invention will be apparent, and may be made by, persons of ordinary skill in the art having reference to this description. It is contemplated that all such changes and additional embodiments are within scope of the invention as claimed below. For example, data on surgical parameters may be provided to a heads-up display via a wired coupling between surgical console and heads-up display unit as opposed to a wireless coupling, there may be a certain type of feedback pre-associated with a surgical parameter such that once surgical parameters are configured the corresponding feedback is also configured, etc.

What is claimed is:

1. A device for presenting information in conjunction with a surgical console, comprising:
    a heads-up display configured to be mounted to a microscope; the heads-up display comprising:
        an eye-piece ring operable to be fitted to or inside an eye-piece of the microscope;
        a body coupled to the eye-piece ring through a translucent solid material, wherein the body of the heads-up display is operable to receive data regarding a set of surgical parameters from a surgical console and present feedback corresponding to each of the set of parameters to a user;
        wherein the feedback corresponding to a first parameter of the set of surgical parameters is visual feedback presented through the eye-piece ring, wherein the visual feedback is transmitted to the eye-piece ring through the translucent solid material coupling the eye-piece ring to the body of the heads-up display; and wherein the eye-piece ring comprises a ring surrounding a transparent region configured to allow light to pass through the eye-piece ring such that the visual feedback may be presented through the ring without impeding light traveling through the transparent region of the ring.

2. The device of claim 1, wherein the heads-up display includes or is communicably coupled to an audio source and wherein the feedback corresponding to a second surgical parameter is audio feedback from the audio source.

3. The device of claim 1, further comprising the surgical console, wherein the set of surgical parameters are selected by the user using the surgical console.

4. The device of claim 3, wherein the feedback corresponding to the first surgical parameter is congruent with an interface used to configure a parameter associated with the first surgical parameter.

5. The device of claim 4, wherein the visual feedback corresponding to the first surgical parameter is color of light.

6. The device of claim 5, wherein the feedback corresponding to a third surgical parameter is visual feedback comprising a mix of colors or a blink pattern with alternating colors of light.

7. The device of claim 5, wherein the first surgical parameter is an estimated instantaneous temperature at an incision.

8. The device of claim 7, wherein the visual feedback corresponding to a second surgical parameter is a blink rate.

9. The device of claim 8, wherein the second surgical parameter is a vacuum level.

10. The device of claim 1, wherein the transparent region comprises a hole.

11. A method for presenting information in conjunction with a surgical console, comprising:
  receiving data regarding a set of surgical parameters from a surgical console at a heads-up display configured to be mounted to a microscope;
  converting at least a portion of the received data into visual feedback corresponding to the set of parameters;
  transmitting the visual feedback through a translucent solid material connecting a body of the heads-up display to an eye-piece ring operable to be fitted to or inside an eye-piece of the microscope; and
  presenting the visual feedback corresponding to the set of parameters to a user through the eye-piece ring; and
  wherein the eye-piece ring comprises a ring surrounding a transparent region configured to allow light to pass through the eye-piece ring such that the visual feedback may be presented through the ring without impeding light traveling through the transparent region of the ring.

12. The method of claim 11, wherein the visual feedback corresponds to a first surgical parameter and wherein the method further comprises presenting audio feedback corresponding to a second surgical parameter.

13. The method of claim 11, wherein the set of surgical parameters are selected by the user using the surgical console.

14. The device of claim 11, wherein the visual feedback further comprises a mix of colors or a blink pattern with alternating colors of light.

15. The method of claim 14, wherein at least one surgical parameter of the set of surgical parameters is an estimated instantaneous temperature at an incision.

16. The method of claim 15, wherein the visual feedback further comprises a varying blink rate.

17. The method of claim 16, wherein at least one surgical parameter of the set of surgical parameters is a vacuum level.

18. The device of claim 11, wherein the transparent region comprises a hole.

19. A device for presenting information in conjunction with a surgical console, comprising:
  a heads-up display mounted to a microscope; the heads-up display comprising an eye-piece ring fitted to or inside an eye-piece of the microscope, wherein the heads-up display further comprises a body coupled to the eye-piece ring through a translucent solid material, wherein the body of the heads-up display receives data regarding a surgical parameter through a wired or wireless connection to a surgical console;
  wherein the heads-up display is configured to present visual feedback corresponding to the surgical parameter to a user by conducting light through the translucent solid material, coupled to the heads up display and the eye-piece ring, to the eye-piece ring that is fitted to or inside the eye-piece of the microscope; and
  wherein the eye-piece ring comprises a ring surrounding a transparent region configured to allow light to pass through the eye-piece ring such that the visual feedback may be presented through the ring without impeding light traveling through the transparent region of the ring.

20. The device of claim 19, wherein the body of the heads-up display further comprises a speaker to produce audio feedback corresponding to the surgical parameter.

21. The device of claim 19, wherein the body of the heads-up display, that receives data regarding the surgical parameter through a wired or wireless connection to a surgical console, is directly connected to the eye-piece ring through the translucent solid material.

22. The device of claim 19, wherein the transparent region comprises a hole.

* * * * *